United States Patent [19]

Dow et al.

[11] Patent Number: 5,498,621

[45] Date of Patent: Mar. 12, 1996

[54] OXAZOLIDINEDIONE HYPOGLYCEMIC AGENTS

[75] Inventors: Robert L. Dow, Waterford; Bernard Hulin, Essex; David A. Clark, East Lyme, all of Conn.

[73] Assignee: Pfizer Inc., New York, N.Y.

[21] Appl. No.: 289,612

[22] Filed: Aug. 12, 1994

Related U.S. Application Data

[63] Continuation of Ser. No. 855,038, filed as PCT/US89/05222, Nov. 13, 1989, abandoned.

[51] Int. Cl.$^6$ .................................................. A61K 31/42
[52] U.S. Cl. .......................... 514/369; 514/375; 514/376; 548/203; 548/204; 548/217; 548/226; 548/235; 548/236
[58] Field of Search .................................. 514/369, 375, 514/376; 548/203, 204, 217, 226

[56] References Cited

U.S. PATENT DOCUMENTS

| | | | |
|---|---|---|---|
| 4,332,952 | 6/1982 | Schnur | 548/226 |
| 4,340,605 | 7/1982 | Kawamatsu et al. | 548/183 |
| 4,342,771 | 8/1982 | Schnur | 546/152 |
| 4,367,234 | 1/1983 | Schnur | 548/226 |
| 4,448,971 | 5/1984 | Schnur | 548/226 |
| 4,617,312 | 10/1986 | Schnur | 548/183 |
| 4,689,336 | 8/1987 | Schnur | 548/227 |
| 4,703,052 | 10/1987 | Eggler et al. | 546/246 |
| 4,725,610 | 2/1988 | Meguro et al. | 548/183 |
| 4,738,972 | 4/1988 | Eggler et al. | 548/183 |
| 4,753,956 | 6/1988 | Schnur | 548/226 |
| 4,791,125 | 12/1988 | Clark | 548/183 |
| 4,897,393 | 1/1990 | Iijima | 514/364 |
| 5,036,079 | 7/1991 | Clark | 514/333 |
| 5,037,842 | 8/1991 | Goldstein | 514/375 |
| 5,089,514 | 2/1992 | Hulin | 514/374 |
| 5,120,754 | 6/1992 | Clark et al. | 514/369 |
| 5,266,582 | 11/1993 | de Nanteuil et al. | 514/369 |
| 5,330,998 | 7/1994 | Clark et al. | 514/369 |
| 5,436,257 | 7/1995 | Fujita | 514/369 |

FOREIGN PATENT DOCUMENTS

| | | |
|---|---|---|
| 0084926 | 8/1983 | European Pat. Off. . |
| 097453 | 1/1984 | European Pat. Off. . |
| 177353 | 4/1986 | European Pat. Off. . |
| 283035A | 9/1988 | European Pat. Off. . |
| 299620A | 1/1989 | European Pat. Off. . |
| 299620 | 1/1989 | European Pat. Off. . |
| 0026686 | 2/1982 | Japan . |
| 1097926 | 4/1989 | Japan . |
| 2083810 | 3/1982 | United Kingdom . |

OTHER PUBLICATIONS

Dow et al. Chem Abstr vol. 114 entry 228799a (1991).
Ross & Glomset, New England Journal of Medicine, 295, 369–377, (1976).
Sohda, et al., I, Chem. Pharm. Bull., 30, 3563–64, (1982) (rest of article not provided, seen).
Sohda, et al., II, Chem. Pharm. Bull., 30, 3580–3600, (1982).
Sohda et al., I, Chem. Pharm. Bull., 1982, 30, 3563–80.

Primary Examiner—Donald G. Daus
Attorney, Agent, or Firm—Peter C. Richardson; Gregg C. Benson; Robert T. Ronau

[57] ABSTRACT

Compounds of the formulae

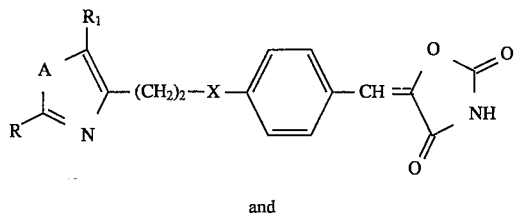

and

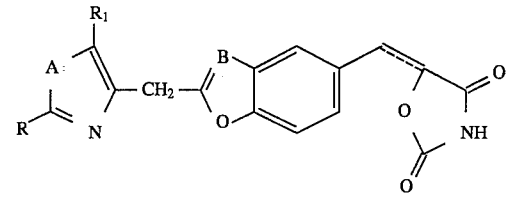

where R is cycloalkyl or aryl; $R_1$ is alkyl, X is O or C=O; A is O or S; and B is N or CH are useful as hypoglycemic agents.

18 Claims, No Drawings

OXAZOLIDINEDIONE HYPOGLYCEMIC AGENTS

BACKGROUND OF THE INVENTION

This is a continuation of application Ser. No. 07/855,038, filed on 01 May 1992 abandoned which is a continuation of International Application No. PCT/US89/05222, filed 13 Nov. 1989, entitled "Oxazolidinedione Hypoglycemic Agents."

The present invention relates to certain compounds of the formulae (I) and (II), depicted below, having utility as hypoglycemic and hypocholesteremic agents, methods for their use and pharmaceutical compositions containing them.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily doses, usually by self injection. Determination of the proper dosage of insulin requires frequent estimations of the sugar in the urine or in the blood. The administration of an excess dose of insulin causes hypoglycemia, with effects ranging from mild abnormalities in blood glucose or coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

Furthermore, atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the the arterial occlusion and tendency toward mural thrombosis and arterial muscular spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at high risk for development or progression of CVD because of this factor. Individuals who possess independent risk factors in addition to hyperlipidemia are at particularly high risk. Such independent risk factors include glucose intolerance, left ventricular hypertrophy hypertension, and being of the male sex. Cardiovascular disease is especially prevalent among diabetic subjects, at least in part because of the existence of multiple independent risk factors. Successful treatment of hyperlipidemia in the general population, and in diabetic subjects in particular, is therefore of exceptional medical importance.

The first step in recommended therapeutic regimens for hyperlipidemia is dietary intervention. While diet alone produces adequate response in some individuals, many others remain at high risk and must be treated further by pharmacological means. New drugs for the treatment of hyperlipidemia are, therefore, of great potential benefit for large numbers of individuals at high risk of developing CVD. Further, successful treatment of both the hyperlipidemia and hyperglycemia associated with the diabetic state with a single therapeutic agent is particularly desirable.

In addition to the hypoglycemic agents cited above, a variety of other compounds have been reported to possess this type of activity, as reviewed by Blank [Burger's Medicinal Chemistry, Fourth Edition, Part II, John Wiley and Sons, N.Y. (1979), pp. 1057–1080].

Schnur, U.S. Pat. No. 4,367,234 discloses hypoglycemic oxazolidinediones of the formula

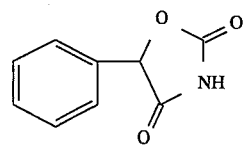

in which the phenyl ring is generally mono- or multi-substituted in the ortho/meta positions. Notably, with the exception of the 4-fluorophenyl analog, the para-substituted derivatives are either inactive or possess a low level of hypoglycemic activity. Schnur, U.S. Pat. Nos. 4,332,952 and 4,342,771 further disclose a variety of similar oxazolidinedione hypoglycemic agents which are alternatively substituted at the 5-position with a heterocyclic group. These include certain furan, thiophene, pyrrole and pyridine derivatives.

Schnur, U.S. Pat. No. 4,617,312 discloses hypoglycemic thiazolidinediones of the formula

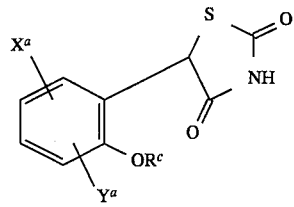

where $R^c$ is lower alkyl, is F, Cl or Br, and $y^a$ is $X^a$ is hydrogen, chloro, lower alkyl or lower alkoxy. Notably, the compounds require ortho-substitution with an alkoxy group, and para-substitution is limited to hydrogen or halogen. Shoda et al. (*Chem. Pharm. Bull.*, 30, 3563 (1982) describe the preparation of a series of 5-[4-(2-methyl- 2-phenylpropoxy)benzyl]thiazolidine-2,4-diones as antidiabetic agents.

Kawamatsu et al., U.S. Pat. No. 4,340,605,disclose hypoglycemic compounds of the formula

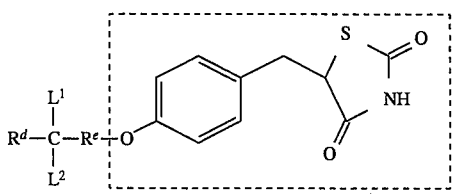

wherein $R^e$ is a bond or lower alkylene and when $R^d$ is an optionally substituted five- or six-membered heterocyclic group including one or two hetero-atoms selected from N, O and S, $L^1$ and $L^2$ may each be defined as hydrogen. Based on the lack of hypoglycemic and plasma triglyceride lowering activity of certain non-ether analogs, it has been suggested that the boxed portion of the structural formula, including the ether oxygen, represents an essential feature for useful activity in this series of compounds; Sohda et al., Chem. Pharm. Bull. Japan, Vol. 30, pp. 3580–3600 (1982).

Sohda et al. also describe the compound of the formula

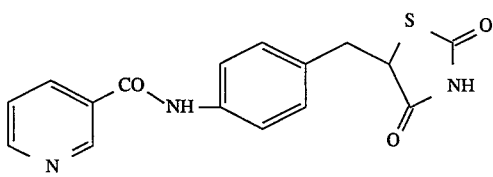

as having weak hypoglycemic and plasma triglyceride lowering activity.

Eggler et al., U.S. Patent 4,703,05discloses hypoglycemic thiazolidinediones of the formula

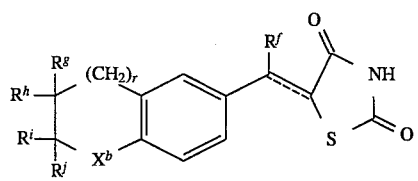

where the dotted line represents an optional bond, $R^f$ is H, methyl or ethyl, $X^b$ is O, S, SO, $SO_2$, $CH_2$, CO, CHOH or $NR^k$, $R^k$ is H or an acyl group and the numerous definitions of $R^g$, $R^h$, $R^i$ and $R^j$ include $R^g$, $R^h$ and $R^i$ as hydrogen or methyl and $R^j$ as optionally substituted phenyl, benzyl, phenethyl or styryl.

Meguro et al., U.S. Pat. No. 4,725,610 disclose a series of hypoglycemic thiazolidinediones of the formula

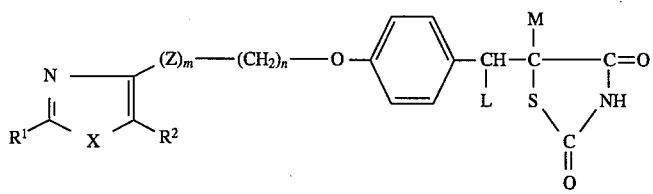

EP 283,035A and EP 299,620A describe benzoxazole and benzofuran linked thiazolidinediones as antidiabetic agents.

SUMMARY OF THE INVENTION

The present invention relates to compounds of formulae (I) and (II)

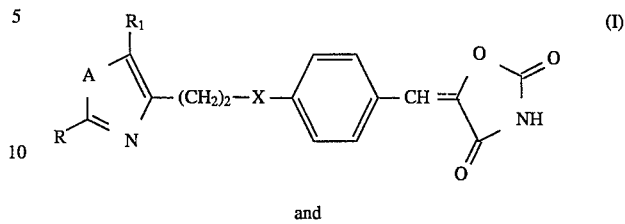

and

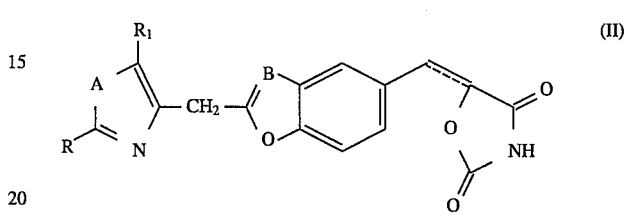

or a pharmaceutically acceptable salt thereof wherein the dotted line represents a bond or no bond; R is cycloalkyl of three to seven carbon atoms, naphthyl, thienyl, furyl, phenyl or substituted phenyl wherein said substituent is alkyl of one to three carbon atoms, alkoxy of one to three carbon atoms, trifluoromethyl, chloro, fluoro or bis(trifluoromethyl); $R_1$ is alkyl of one to three carbon atoms; X is O or C=O; A is O or S; and B is N or CH.

A preferred group of compounds are those of formula I wherein the dotted line represents no bond, $R_1$ is methyl, X is O and A is O. Especially preferred within this group are the compounds where R is phenyl, 2-naphthyl and 3,5-bis(trifluoromethyl)phenyl.

A second group of preferred compounds are those of formula II wherein the dotted line represents no bond, $R_1$ is methyl and A is O. Especially preferred within this group are compounds where B is CH and R is phenyl, p-tolyl, m-tolyl, cyclohexyl and 2-naphthyl. Also especially preferred is the compound where B is N and R is phenyl.

The present invention also includes pharmaceutical compositions for use in hypoglycemic and hypercholesterolemic mammals which comprises blood sugar lowering and blood cholesterol lowering amounts, respectively, of compounds of formulae I and II with a suitable carrier.

Also included are methods for lowering blood glucose or blood cholesterol in a hyperglycemic or hypercholesterolemic mammal, respectively, which comprises administering to said mammal a blood glucose lowering or blood cholesterol lowering amount of a compound of formula I or II.

The expression "pharmaceutically-acceptable salts" is intended to define but not limited to such base salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl-1,3-propanediol) and procaine. Also included in the definition are such acid addition salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

DETAILED DESCRIPTION OF THE INVENTION

The compounds of formula I wherein the dotted line represents no bond are prepared by two procedures.

The first procedure or process comprises the removal of a triphenylmethyl moiety from the 3-position of the oxazolidinedione shown as follows:

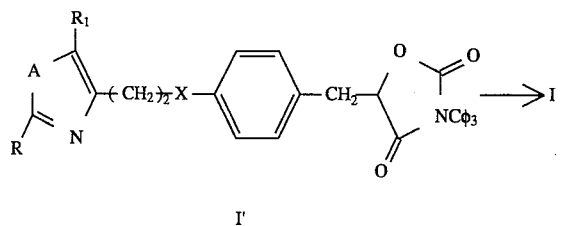

The removal of the triphenylmethyl group is achieved by treating the starting material with trifluoroacetic acid at room temperature until the reaction is complete. Reaction time is generally 30–60 minutes. The desired product is obtained by quenching the reaction mixture in water followed by extraction of the product with a water-immiscible solvent, such as ethyl acetate. The product can be purified by conventional means such as recrystallization or chromatography.

The starting reagents leading to I'0 can be prepared by methods herein described and comprise either a coupling of an alcohol (X=O) and a phenol, such as

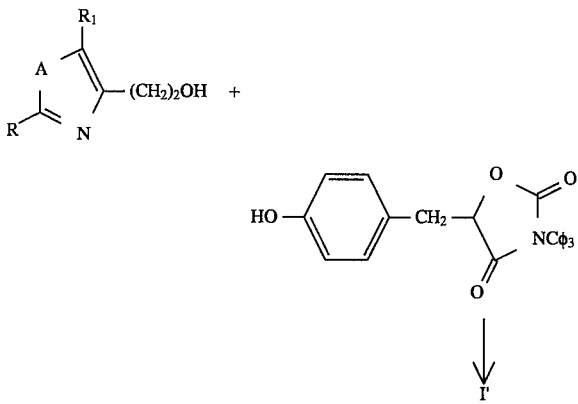

or the alkylation of 3-triphenylmethyl-2,4-oxazolidinedione, such as

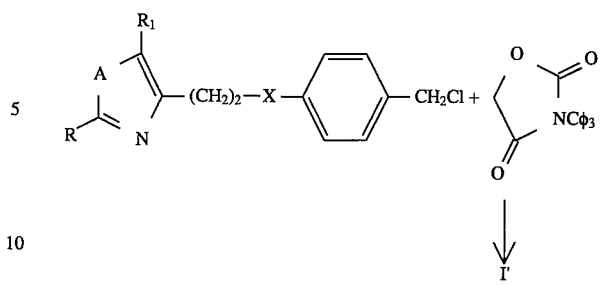

The second process leading to the subject compounds of formula I wherein the dotted line represents no bond comprises the reduction of the compounds of formula I wherein the dotted line represents a bond.

The starting olefinic products are active hypoglycemic agents, but also serve as intermediates for preparation of the corresponding reduced compounds of formula (I) wherein the dotted line represents no bond. While the reduction of these olefins may be carried out by employing a number of reducing agents which are known to reduce carbon-to-carbon double bonds, the preferred methods employ hydrogen in the presence of a noble metal catalyst, sodium amalgam in methanol, or zinc in acetic acid.

When the reduction step is carried out employing hydrogen in the presence of a noble metal catalyst, a convenient method for carrying out this transformation is to stir or shake a solution of the olefinic compound of the formula (I) wherein the dotted line represents a bond in a reaction-inert solvent under an atmosphere of hydrogen, or hydrogen mixed with an inert diluent such as nitrogen, in the presence of a sulfur resistant noble metal hydrogenation catalyst. Suitable solvents for this reaction are those which substantially dissolve the starting compound but which do not themselves suffer hydrogenation or hydrogenolysis. Examples of such solvents include ethers such as diethyl ether, tetrahydrofuran, dioxane and 1,2-dimethoxyethane; low molecular weight amides such an N,N-dimethylformamide, N-N-dimethylacetamide and N-methylpyrrolidone; and lower alkyl carboxylic acids such as formic, acetic, propionic and isobutyric acid. Especially preferred such solvents are tetrahydrofuran and acetic acid. Hydrogenation is particularly preferred when W is other than S or SO.

Introduction of the hydrogen gas into the reaction medium is usually accomplished by carrying out the reaction in a sealed vessel, containing the olefinic compound, solvent, catalyst and hydrogen. The pressure inside the reaction vessel can vary from about 1 to about 100 kg/cm². The preferred pressure range, when the atmosphere inside the reaction vessel is substantially pure hydrogen, is from about 2 to about 5 kg/cm². The hydrogenation is generally run at a temperature of from about 0° to about 60° C., and preferably from about 25° to about 50° C. Utilizing the preferred temperature and pressure values, hydrogenation generally takes place in a few hours, e.g., from about 2 hours to about 20 hours. The preferred noble metal catalysts used in this hydrogenation reaction are the type of agents known in the art for this kind of transformation, for example, palladium, platinum and rhodium. A sulfur resistant palladium catalyst is preferred because such catalysts are not readily poisoned by sulfur. The catalyst is usually present in an amount from about 0.01 to about 25 weight-percent, and preferably from about 0.1 to about 10 weight-percent, based on the olefinic compound. It is often convenient to suspend the catalyst on an inert support; a particularly convenient catalyst is palladium suspended on an inert support such as carbon.

When the hydrogenation of the methylene double bond is substantially complete, the desired product of formula (I) wherein the dotted line is no bond is then isolated by standard methods, e.g., the catalyst is recovered by filtration, the solvent evaporated and the product purified, if desired, by well known methods such as crystallization or by chromatography.

Those compounds of formula I where the dotted line represents a bond are prepared by treating the corresponding 2-thio-2,4-oxazolidinedione of the formula

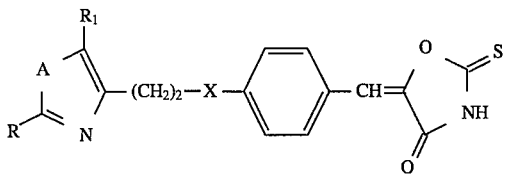

with an oxidizing agent in a reaction-inert solvent such as dimethylformamide. The preferred oxidizing agents are peracids, such as m-chloroperbenzoic acid or mono-peroxyphthalic acid and hydrogen peroxide under basic conditions. The reaction is usually carried out at room temperature for a period of 1.5–2 hours using an equimolar amount plus a 20–30% excess of the oxidizing reagent. The product is isolated by adding the reaction mixture to water followed by extraction with a water-immiscible solvent such as ethyl acetate. Purification can be carried out by recrystallization or chromatography.

The 2-thio-2,4-oxazolidinedione shown above is prepared by the reaction of the corresponding benzaldehyde derivative with an excess of 2-thio-2,4oxazolidinedione and a 2–4 fold molar excess of anhydrous sodium acetate. The resulting mixture is heated at a temperature high enough to effect melting, generally about 140°–170° C., at which temperature the reaction is substantially complete in from about 5 to 60 minutes. The desired olefin is then isolated, for example, by mixing with water and filtration, to obtain the crude product, which is purified, if desired, e.g., by crystallization or by standard chromatographic methods.

Those compounds of formula II where the dotted line represents no bond are prepared by the reduction of the corresponding olefin as was described in the second process leading to the compounds of formula I where the dotted line represents no bond. The reaction conditions are the same as previously described as are the methods for isolation and purification.

The process conditions leading to II wherein the dotted line represents a bond are also the same as those providing for the synthesis of the olefin of formula I, wherein the corresponding 2-thio-2,4-oxazolidinedione is treated with an oxidizing agent. Again, the reaction parameters are the same, as are the means of isolation and purification.

In addition, there is one further process for preparing compounds of formula II where B is N and the dotted line represents no bond. This comprises reacting a compound of the formula

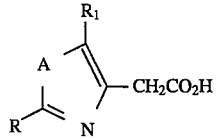

with an o-aminophenol of the formula

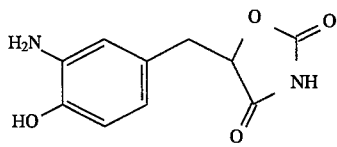

under dehydrating conditions. In practice, equimolar amounts of the reactants depicted above, where A, R and $R_1$ are as defined, are heated in a high boiling, reaction-inert solvent, such as o-dichlorobenzene, in the presence of excess phosphorus pentoxide and bis(trimethylsilyl)ether at 125°–150° C. for 2–3 hours. The product is isolated by quenching the reaction in water followed by extraction with a water immiscible solvent. Purification is by recrystallization or chromatography.

The starting reagents for the processes described are contained herein or are prepared by reactions known to those skilled in the art.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The present compounds of the formula (I) are readily adapted to clinical use as hypoglycemic or hypocholesterolemic agents. The activity required for the former clinical use is defined by the test for hypoglycemic effect in ob/ob mice by the following procedure:

Five to eight week old C57 BL/6J-ob/ob mice (obtained from Jackson Laboratory, Bar Harbor, Me.) were housed five per cage under standard animal care practices. After a one week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (5–50 mg/kg), a positive control (50 mg/kg) of ciglitazone; U.S. Pat. No. 4,467,902; Sohda et al., Chem. Pharm. Bull., vol. 32, pp. 4460–4465, 1984), or vehicle. All drugs were administered in a vehicle consisting of 0.25% w/v methyl cellulose. On day 5, the animals were weighed again and bled (via the ocular route) for blood metabolite levels. The freshly collected samples were centrifuged for two minutes at 10,000× g at room temperature. The supernatant was analyzed for glucose, for example, by the ABA 200 Bichromatic Analyzer™, using the A-gent™ glucose UV reagent system* (hexokinase method) using 20, 60 and 100 mg/dl standards. Plasma glucose was then calculated by the equation, Plasma glucose (mg/dl)=Sample value×5×1.67=8.35×Sample value where 5 is the dilution factor and 1.67 is the plasma hematocrit adjustment (assuming the hematocrit is 40%). ™ A registered trademark of Abbott Laboratories, Diagnostics Division, 820 Mission Street, So. Pasadena, Calif. 91030.

*A modification of the method of Richterich and Dauwalder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

Studies such as that described below demonstrate that the compounds of formula (I) effect the lowering of serum cholesterol levels in mammals.

Female mice (strain C57Br/cd J), obtained from Jackson Laboratories, Bar Harbor, Me., are used at age 8–12 weeks, following 2–4 weeks acclimation having free access to water and standard laboratory chow. Animals are divided randomly into three groups of 6–7 animals. All three groups are placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin; permitted to feed ad lib for 18 days; and dosed daily at 9–11 a.m. for the final 5 days by oral gavage, the control group with 5 ml/kg of vehicle (0.1% aqueous methyl cellulose) and the test groups with the compound under study at a dose range of 0.1–20 mg/kg/day in vehicle. After the fourth day of dosing, the animals are fasted overnight, starting at 5 p.m. The following morning a fifth and final dose of the compound is administered to the test groups and, three hours later, the animals are sacrificed by decapitation. Blood from the body trunk is collected and allowed to clot, and the serum assayed enzymatically, using an Abbott VP automated analyzer, for HDL cholesterol, LDL and VLDL cholesterol, and total cholesterol. Whether judged on the basis LDL+ VLDL cholesterol levels, total cholesterol levels or the ratio of LDL+VLDL/HDL, the compounds of this invention generally show favorable result in lowering cholesterol levels.

The present compounds of the formulae (I) and (II) are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or pharmaceutically acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. The injectable solutions prepared in this manner can then be administered intravenously, intraperitoneally, subcutaneously, or intramuscularly, with intramuscular administration being the preferred parenteral route in man.

The present invention is illustrated by the following Examples. However, it should be understood that the invention is not limited to the specific details of these examples.

EXAMPLE 1

5-(4-[2-Cyclohexyl-5-methyloxazol-4-ylethoxy] benzyl)-2,4-oxazolidinedione (I: R=$C_6H_{11}$; $R_1$=$CH_3$; A=O; and X=O)

A. Ethyl alpha-cyclohexylcarbonylaminoacetoacetate

To a suspension of 23.6 g of ethyl alpha-aminoacetoacetate hydrochloride in 450 ml of chloroform cooled to 0° C. was added 19.52 ml of cyclohexylcarbonyl chloride. After 20 minutes at 0° C. 36 ml of triethylamine was added dropwise over a period of 30 minutes. The reaction mixture was allowed to warm to room temperature, was washed with water (2×300 ml) and brine (300 ml) and dried over magnesium sulfate. Removal of the solvent in vacuo gave 35.1 g of an oil which on chromatographing on 400 g of silica gel (hexane-ethyl acetate; 7.5:2.5; v:v) gave 13.9 g of product, m.p. 74°–75° C.

B. Ethyl 2-cyclohexyl-5-methyloxazole-4-carboxylate

To a solution of 260 mg of the product of Example 1A in 1.5 ml of dry dimethylformamide was added 460 mg of phosphorus oxychloride and the resulting solution heated at 90° C. for 1.5 hours. The reaction mixture was cooled, poured onto 20 g of ice and subsequently neutralized with 12 ml of a saturated aqueous sodium bicarbonate solution. The mixture was extracted with ethyl acetate and the organic phase washed with water (2×20 ml) and a brine solution and dried over sodium sulfate. Removal of the solvent under vacuum gave 210 mg of crude product which was purified by chromatographing on 30 g of silica gel (hexane-acetone; 8.5:1.5; v:v), 140 mg.

C. 2-Cyclohexyl-4-hydroxymethyl-5-methyloxazole

To 32 ml of a 1M solution of lithium aluminum hydride in tetrahydrofuran under a nitrogen atmosphere and cooled to 0° C. was added dropwise 7.6 g of the product of Example 1B in 64 ml of dry tetrahydrofuran. When the addition was complete, the reaction mixture was allowed to stir at 0° C. for 25 minutes and was then treated with 1.42 ml of water, 1.42 ml of 20% aqueous sodium hydroxide and 50 ml of water. The slurry was filtered and the solvent removed to give 6.02 g of product which was employed in the next step without further purification.

D. 2-Cyclohexyl-4-chloromethyl-5-methyloxazole

To a solution of 6.0 g of the product of Example 1C in 50 ml of dry methylene chloride under nitrogen and cooled to 0° C. was added 30 ml of thionyl chloride in 10 ml of methylene chloride dropwise over a period of 45 minutes. The reaction mixture was stirred 30 minutes following the addition and was then concentrated in vacuo to a dark residue which was dissolved in 600 ml of ethyl acetate. The resulting solution was washed with a saturated sodium bicarbonate solution (3×150 ml), water and finally a brine solution. The organic phase was dried over magnesium sulfate and concentrated to 5.18 g of a dark brown syrup which was used in the next step without further purification.

E. 2-Cyclohexyl-4-cyanomethyl-5-methyloxazole

Under a nitrogen atmosphere 3.15 g of potassium cyanide was added portionwise at room temperature to a solution of 5.16 g of the product of Example 1D in 30 ml of dimethylsulfoxide. The reaction mixture was stirred at room temperature for 2.5 hours and was then poured into 300 ml of water. The aqueous mixture was extracted with ethyl acetate (400, 300 ml) and the combined extracts were washed with water (2×400 ml) and a brine (250 ml) solution, and dried over sodium sulfate. Removal of the solvent gave 4.65 g of the product as a brown oil. The product was used without further purification.

F. 2-Cyclohexyl-4-carboxymethyl-5-methyloxazole

To 5.2 ml of ethanol and 5.4 ml of a 2N sodium hydroxide solution was added 4.0 g of the product of Example 1E, and the resulting mixture heated to reflux for 35–45 minutes. The resulting solution was cooled and poured into 16.6 ml of 2N hydrochloric acid and cooled further in an ice bath. The cold solution was extracted with ethyl acetate (2×75 ml) and the combined extracts backwashed with water (2×30 ml) and a saturated brine solution and dried over sodium sulfate. Concentration of the solution gave 3.4 g of the desired product as a dark brown oil.

G. 2-Cyclohexyl-4-hydroxyethyl-5-methyloxazole

To a solution of 3.35 g of the product of Example 1F in 30 ml of dry tetrahydrofuran cooled to 0° C. and under a nitrogen atmosphere was added 45 ml of a 1M solution of boron trihydride.tetrahydrofuran complex in anhydrous tetrahydrofuran over a period of about one hour. The reaction was quenched by adding 25 ml of a mixture of tetrahydrofuran and water (1:1, v:v) followed by 20 ml of a 1N sodium carbonate solution. Water (300 ml) and ethyl acetate (300 ml) were added and organic layer was separated. The aqueous layer was separated and extracted further with ethyl acetate (2× 100 ml). The extracts were combined, dried over sodium sulfate and concentrated in vacuo to give 3.34 g of a dark oil. Flash chromatography on 400 g of silica gel using hexane-ethyl acetate; 3.8:6.2; v:v) gave 780 mg of pure product.

H. 3-Triphenylmethyl-5-(4-[2-cyclohexyl-5-methyloxazol-4-ylethoxy]benzyl)-2,4-oxazolidinedione The product of Example 1G (870 mg), 2.0 g of 3-triphenylmethyl-5-(p-hydroxybenzyl)-2,4-oxazolidinedione and 1.31 g of triphenylphosphine were combined in 25 ml of dry tetrahydrofuran under a nitrogen atmosphere. To the resulting homogeneous solution was added 796 mg of diethyl azodicarboxylate dropwise at room temperature. After stirring for 27 hours, the reaction mixture was quenched with water (100 ml) and the solution extracted with ethyl acetate. The ethyl acetate layer was washed with a brine solution and dried over sodium sulfate. Removal of the solvent in vacuo gave a crude residue, which was chromatographed on silica gel (280 g) (toluene-dioxane; 9.4:0.6; v:v) to give 1.15 g of product.

I. 5- (4-[2-Cyclohexyl-5-methyloxazol-4-ylethoxy] benzyl)-2,4-oxazolidinedione

The product of Example 1H (830 mg) was added to 10 ml of trifluoroacetic acid and the reaction mixture was stirred at room temperature under nitrogen for 30 minutes. The reaction mixture was diluted with 200 ml of ethyl acetate and the resulting solution washed with water (4×40 ml) and a brine solution (2×25 ml), and dried over sodium sulfate. The solvent was removed in vacuo and the residue chromatographed on 80 g of silica gel (toluene-dioxane; 8:2; v:v) to give 465 mg of the desired product.

The NMR (300 MHz, CDCl$_3$) delta, showed absorption at 8.59 (bs, 1H), 7.03 (d, 2H), 6.71 (d, 2H), 4.97 (t, 1H), 4.0 (t, 2H), 3.12 (ABq, 2H), 2.80 (t, 2H), 2.78 2.64 (m, 1H), 2.19 (s, 3H) and 2.0–1.12 (m, 10H).

EXAMPLE 2

Employing the procedures of Example 1 and starting with the appropriate reagents, the following compounds were prepared:

| R | $R_1$ | A | X | m.p. °C. | NMR (300 MHz) delta |
|---|---|---|---|---|---|
| CF$_3$-phenyl-CF$_3$ (3,5-bis(trifluoromethyl)phenyl) | CH$_3$ | O | O | 167–170 | (DMSO-d$_6$) 8.35 (s, 2H), 8.18 (s, 1H), 7.04 (d, 2H), 6.81 (d, 2H), 5.11 (t, 1H), 4.15 (t, 2H), 3.10–2.84 (m, 4H) and 2.36 (s, 3H). |

Analysis calculated for C$_{24}$H$_{18}$N$_2$O$_5$F$_6$:

C, 54.6; H, 3.4; N, 5.3%.
Found: C, 53.8; H, 3.3; N, 5.2%.

-continued

[Structure: oxazole ring with R, R₁, A substituents connected via (CH₂)₂-X-phenyl-CH₂-oxazolidinedione group]

| R | R₁ | A | X | m.p. °C. | NMR (300 MHz) delta |
|---|----|----|----|----------|---------------------|
| 2-naphthyl | CH₃ | S | O | 182–183 | (DMSO-d₆) 8.32 (s, 1H), 8.0–7.82 (m, 4H), 7.56–7.42 (m, 2H), 7.03 (d, 2H), 6.82 (d, 2H), 5.12 (t, 1H), 4.24 (t, 2H), 4.42–2.86 (m, 4H) and 2.40 (s, 3H). |

Analysis calculated for $C_{26}H_{22}N_2O_4S$:

C, 68.1; H, 4.8; N, 6.1%.
Found:        C, 59.0; H, 4.0; N, 5.0%.

EXAMPLE 3

5-(4-[Cyclohexyl-5-methyloxazol-4-ylethoxy]benzyl)-2,4-oxazolidinedione Sodium Salt To a solution of 465 mg of the product of Example 1 in 1.5 ml of dry tetrahydrofuran under nitrogen was added 137.5 mg of sodium trimethylsilanolate in one portion. The reaction mixture was allowed to stir for 2 hours at room temperature and was then concentrated to dryness under vacuum. The residue was triturated with 20 ml of diethyl ether, filtered, washed with ether and dried in vacuo, 391 mg, m.p. 209°–214° C. dec.

EXAMPLE 4

5-(4-[2-Phenyl-5-methyloxazol-4-ylethoxy]benzyl)-2,4-oxazolidinedione (I: R=C₆H₅; R₁=CH₃; A=O; and X=O)

A. 4-(2-Phenyl-5-methyloxazol-4-ylethoxy) benzaldehyde

A mixture of 6.0 g of 4-(2-phenyl-5-methyloxazol4-ylethoxy)benzonitrile (prepared by reacting p-fluorobenzonitrile with 2-phenyl-4-hydroxyethyl-5-methyloxazole), 6.0 g of Raney nickel alloy and 100 ml of 70% formic acid was heated to reflux for 2 hours. The reaction was cooled and the solids filtered and washed with ethyl acetate. The washings and formic acid filtrate were combined and concentrated in vacuo to an oil. The residue was treated with water (100 ml) and extracted with ethyl acetate (3×100 ml). The extracts were combined and washed with water until the pH of the washings was 7. The extracts were washed with a brine solution, dried over sodium sulfate and concentrated to an oil, which on chromatographing on 250 g of silica gel (ethyl acetate-hexane; 30:70; v:v) gave 5.08 g of product, m.p. 79°–81° C.

B. 4-(2-Phenyl-5-methyloxazol-4-ylethoxy)benzyl alcohol

Using the procedure of Example 1C, 2.0 g of the product of Example 4A and 6.51 ml of a 1.0M solution of lithium aluminum hydride in diethyl ether gave 1.69 g of the product as a waxy solid, m.p. 110°–113° C.

C. 3-Triphenylmethyl-2,4-oxazolidinedione

To a solution of 600 mg of 2,4-oxazolidinedione and 601 mg of triethylamine in 7.0 ml of chloroform was added 1.66 g of triphenyl chloromethane and the reaction mixture stirred at room temperature for 30 minutes. The resulting mixture was dissolved in 250 ml of ethyl acetate and washed with water (3×50 ml) and brine (2×20 ml) and dried over sodium sulfate. Removal of the solvent gave 1.8 g of the desired product.

D. 4-(2-Phenyl-5-methyloxazol-4-ylethoxy)benzyl chloride

To a solution of 1.8 g of the product of Example 4B in 10 ml of tetrahydrofuran cooled in an ice bath was added 2.5 ml of concentrated hydrochloric acid and the reaction mixture was heated until a solution resulted. The reaction was allowed to proceed at room temperature for 2 hours, at which time 1.0 ml of additional acid was added. After stirring 30 minutes at room temperature, 1.0 g of calcium chloride was added and the stirring continued for 70 minutes. The reaction mixture was diluted with 150 ml of ethyl acetate and the resulting solution washed with water (2×75 ml) and a brine solution (1×30 ml). The organic phase was separated, dried over sodium sulfate and concentrated in vacuo to give 1.65 g of the desired product, m.p. 88°–90° C.

E. 3-Triphenylmethyl-5-(4-E2-phenyl-5-methyloxazol-4-ylethoxy]benzyl)-2,4-oxazolidinedione To 728 mg of the product of Example 4D in a 25 ml round-bottom flask under a nitrogen atmosphere was added 5.0 ml of a 2.0M solution of magnesium methyl carbonate in dimethylformamide and the resulting solution heated to 85° C. for 40 minutes. The resulting orange red solution was then added to a 25 ml 3-necked flask containing 800 mg of the product from Example 4D. The resulting solution was heated under nitrogen at 85° C. for 3 hours. An additional 0.5 equivalent of methyl magnesium anion was prepared and added to the reaction mixture and the reaction heated overnight at 50° C. The reaction was poured into 50 g of ice and 20 ml of 1.0M hydrochloric acid and the mixture allowed to stir for 10 minutes. Ethyl acetate (2×100 ml) was used to extract the aqueous slurry. The extracts were combined, washed with water (2×50 ml) and a brine solution (2×50 ml) and dried over sodium sulfate. Removal of the solvent gave an orange oil which was chromatographed on 180 g of silica gel packed in ethyl acetate-hexane (20%:80%; v:v) using the same ratio of solvents for the elution. This provided an orange oil which was discarded.

Further elution with the same solvents (30%:70%; v:v) provided 650 mg of the desired product as an oily orange solid. This was used without further purification.

F. 5-(4-[2-Phenyl-5-methyloxazol-4-ylethoxy]- benzyl)-2,4-oxazolidinedione

The product of Example 4E (240 mg) was added to 0.5 ml of trifluoroacetic acid and the reaction mixture heated at 60° C. for 20 minutes. The reaction mixture was diluted with 50 ml of ethyl acetate and the organic solution extracted with water (2×30 ml) and a brine solution (1×20 ml) and dried over sodium sulfate. Removal of the solvent gave 208 mg of crude product which on chromatographing over 50 g of silica gel (ethyl acetate/hexane—30%/70% and then 50%/50%—v:v) gave 74 mg of an off-white solid, m.p. 163°–165° C. Mass spectra confirms the product identity.

Employing the procedures of Example 4 and starting with the appropriate reagents, the following compounds were prepared:

5-(4-[2-beta-Naphthyl-5-methyloxazol-4-ylethoxy]benzyl)-2,4-oxazolidinedione, m.p. 173°–175° C. (dec.) (I: R=beta-$C_{10}H_7$; $R_1$=$CH_3$; A=O; and X=O) and 5-(4-[2-fur-2-yl-5-methyloxazol-4-ylethoxy]benzyl)-2,4-oxazolidinedione, m.p. 148°–151° C. (I: R=2-$C_4H_3O$; $R_1$=$CH_3$; A=O; and X=O).

EXAMPLE 5

5-(4-[2-Phenyl-5-methyloxazol-4-ylpropionyl]benzyl)-2,4-oxazolidinedione (I: R=$C_6H_5$; $R_1$=$CH_3$; A=O; and X=C=O)

A. 5-(4-[2-Phenyl-5-methyloxazol-4-ylpropionyl]benzylidene)-2-thio-2,4-oxazolidinedione A mixture of 530 mg of 4-(2-phenyl-5-methyloxazol-4-ylpropionyl)benzaldehyde, 292 mg of 2-thio-2,4-oxazolidinedione and 409 mg of sodium acetate in 3 ml of glacial acetic acid was heated to reflux 2.5 hours. An additional 40 mg of sodium acetate was added and the heating continued for 30 minutes. The reaction mixture was poured into water and the product extracted with ethyl acetate (150 ml). The organic phase was washed with water (2×75 ml) and a brine solution (2×50 ml), dried over sodium sulfate and concentrated to an orange oil. Trituration of the residue with methanol (3×25 ml) gave 223 mg of solid product.

B. 5-(4-[2-Phenyl-5-methyloxazol-4-ylpropionyl]benzylidine)- 2,4-oxazolidinedione To a solution of 223 mg of the product of Example 5A in 4 ml of dimethylformamide, chilled in ice, was added 150 mg of m-chloroperbenzoic acid. The resulting reaction mixture was allowed to stir at room temperature for 2 hours and was then diluted with 150 ml of diethyl ether. The organic solution was washed with water (3×50 ml) and a brine solution (2× 50 ml) and dried over sodium sulfate. Removal of the solvent in vacuo gave a yellow-orange solid which was recrystallized from methanol, 103 mg.

C. 5-(4-[2-Phenyl-5-methyloxazol-4-ylpropionyl]benzyl)-2,4-oxazolidinedione

A mixture of 103 mg of the product of Example 5B and 40 mg of 10% of a sulfur resistant palladium-on-charcoal catalyst in 5 ml of dry tetrahydrofuran was shaken in a hydrogen atmosphere for 15 hours at a pressure of 40 psi. The catalyst was filtered through celite and the filtrate concentrated to a white solid, 69 mg. The product was further purified by chromatographing on 50 g of silica gel (acetone-hexane; 30%–70%; v:v), 35 mg, m.p. 198°–200° C.

EXAMPLE 6

5-(4-[2-p-Methoxyphenyl-5-methyloxazol-4-ylethoxy]benzyl)-2,4-oxazolidinedione (I: R=p-$CH_3OC_6H_4$; $R_1$=$CH_3$; A=O; and X=O)

A. 2-p-Methoxyphenyl-4,5-dimethyloxazole N-oxide

Dry hydrogen chloride was bubbled through a solution of 13.5 g of 2,3-butanedione monoxime and 20 g of p-methoxybenzaldehyde in 45 ml of acetic acid and cooled in an ice bath for 30 minutes. The resulting slurry was added to 250 ml of diethyl ether and the solids filtered. The solids were washed with ether and added to 200 ml of water. The pH of the aqueous suspension was adjusted to pH 12 with concentrated ammonium hydroxide and extracted with 600 ml of chloroform. The organic phase was washed with water (2×200 ml) and a brine solution (1×100 ml) and was dried over sodium sulfate. Removal of the solvent in vacuo gave 28.3 g of the desired product, m.p. 138°–140° C.

B. 2-p-Methoxyphenyl-4-chloromethyl-5-methyloxazole

To a cold solution of 28.2 g of the product of Example 6A in 100 ml of chloroform was added slowly 21.7 g of phosphorus oxychloride in 170 ml of chloroform. Following the addition, the reaction was refluxed for 30 minutes and was then cooled in an ice bath. Concentrated ammonium hydroxide was slowly added to the cold organic solution until the pH was about 10. The resulting slurry was washed with water (3×150 ml) and a brine solution (2×100 ml) and the organic phase dried over sodium sulfate. Removal of the solvent in vacuo gave 28.6 g of a yellow-brown solid. The residue was extracted with 400 ml of hot hexane. The hexane was decanted from a dark tan and concentrated to about 100 ml and the solids allowed to crystallize, 13.23 g.

C. 2-p-Methoxyphenyl-4-cyanomethyl-5-methyloxazole

A mixture of 4.0 g of the product of Example 6B and 2.19 g of potassium cyanide in 17 ml of dimethylsulfoxide was stirred under a nitrogen atmosphere at room temperature for 3 hours. The reaction mixture was poured into 50 ml of water and the product extracted with diethyl ether (2×100 ml). The extracts were combined, washed with water (2×100 ml) and a brine solution (1×50 ml) and dried over sodium sulfate. Removal of the solvent gave 3.71 g of desired the product.

D. 2-p-Methoxyphenyl-4-carboxymethyl-5-methyloxazole

Starting with 3.5 g of the product of Example 6C, 35 ml of 2.0N aqueous sodium hydroxide solution and 35 ml of ethanol and following the procedure of Example 1F 3.56 g of the desired product was isolated.

E. 2-p-Methoxyphenyl-4-hydroxyethyl-5-methyloxazole

Using the procedure of Example 1G, 3.56 g of the product of Example 6D and 14.5 ml of 1.0M solution of lithium aluminum hydride (diethyl ether) in 15 ml of dry tetrahydrofuran gave, after 1 hour at room temperature, 1.12 g of the desired product.

F. 4-(2-p-Methoxyphenyl-5-methyloxazol-4-ylethoxy)benzonitrile

To a cold solution of 1.12 g of the product of Example 6E and 989 mg of p-fluorobenzonitrile in 10 ml of dry tetrahydrofuran under a nitrogen atmosphere was added 268 mg of 60% sodium hydride in oil. The reaction was stirred at 0° C. for 30 minutes and overnight at room temperature. The reaction mixture was diluted with water (50 ml), acidified with 1N hydrochloric acid to pH 2 and extracted with ethyl acetate (2×100 ml). The organic extracts were combined, washed with water (1×50 ml) and a brine solution (1×50 ml) and dried over sodium sulfate. Removal of the solvent under vacuum gave 2.0 g of a brown oil which crystallized under high vacuum. The crude material, on chromatographing on silica gel (ethyl acetate-hexane; 30%–70%; v:v) gave 800 mg of pure product.

G. 4-(2-p-Methoxyphenyl-5-methyloxazol-4-ylethoxy)benzaldehyde

A mixture of 400 mg of the product of Example 6F and 400 mg of a 50% aluminum-nickel alloy in 15 ml of 70% formic acid was heated to reflux for 1.5 hours. The reaction was cooled and the solids filtered. The residue was washed with ethyl acetate and the washings combined with the original filtrate. The combined filtrate and washings were extracted with 150 ml of ethyl acetate. The organic phase was separated, washed with water (1×100 ml), a brine solution (2×75 ml), a 1.0N aqueous sodium hydroxide solution (2×100 ml) and water (1×50 ml) and dried over sodium sulfate. Removal of the solvent gave 370 mg of product as a yellow oil.

H. 5-(4-[2-p-Methoxyphenyl-5-methyloxazol-4-ylethoxy] benzylidene)- 2-thio-2,4-oxazolidinedione Using the procedure of Example 5A 370 mg of the product of Example 6G, 193 mg of 2-thio-2,4-oxazolidinedione and 271 mg of anhydrous sodium acetate in 3 ml of glacial acetic acid gave 113 mg of the desired product as a light brown solid.

I. 5-(4-[2-p-Methoxyphenyl-5-methyloxazol-4-ylethoxy] benzylidene)- 2,4-oxazolidinedione Using the procedure of Example 5B but employing 113 mg of the product of Example 6H, 0.26 ml of 30% hydrogen peroxide and 2.6 ml of a solution composed of 600 mg of potassium hydroxide, 1.5 ml of water and 9 ml of methanol gave 40.7 mg of the desired material.

J. 5-(4-[2-p-Methoxyphenyl-5-methyloxazole-4-ylethoxy] benzyl)- 2,4-oxazolidinedione Employing the procedure of Example 5C, 40 mg of the product of Example 6I and 40 mg of sulfur resistant 10% palladium-on-charcoal in 3 ml of dry tetrahydrofuran gave 20.2 mg of product, m.p. 141°–143° C.

Analysis calculated for $C_{23}H_{22}O_6N_2$:
C, 65.4; H, 5.3; N, 6.6%. Found: C, 65.1; H, 5.1; N, 6.3%.

EXAMPLE 7

5-(2-[2-Phenyl-5-methyloxazol-4-ylmethyl]benzofur-5-ylmethyl)-2,4-oxazolidinedione (II: R=$C_6H_5$; $R_1$=$CH_3$;A=O; and B=-CH=)

A. 2-(2-Phenyl-5-methyloxazol-4-ylcarbonyl-5bromobenzofuran

To a slurry of 294 g of 5-bromosalicylaldehyde in 3 liters of dry ethanol was added 79.06 g of sodium methoxide and the mixture allowed to stir for 20 minutes. To the resulting yellow slurry was added 410 g of 2-phenyl-4-bromoacetyl-5-methyloxazole and the slurry heated to 78° C. for 2 hours. An additional 50 mg of sodium methoxide was added and heating continued overnight under a nitrogen atmosphere. The reaction was cooled and the solids filtered and washed with ethanol, 393 g, m.p. 212°–213° C.

B. 2-(2-Phenyl-5-methyloxazol-4-ylhydroxymethyl) 5-bromobenzofuran

To a slurry of 265.44 g of the product of Example 7A in 2.1 liters of tetrahydrofuran was added 2.5 liters of absolute methanol and the slurry cooled in an ice bath. Sodium borohydride (26.3 g) was added in four portions over a period of 15 minutes. After stirring in the cold for 30 minutes, the reaction mixture was allowed to warm to room temperature. After hour the solvent was removed in vacuo and the residue treated with 3 liters of water. The solids were filtered, washed with water and dried in vacuo, 221.48 g, m.p. 152°–154° C.

C. 2-(2-Phenyl-5-methyloxazol-4-ylmethyl)-5-bromobenzofuran

Trifluoroacetic acid (7 ml) was added to 1.35 g of the product of Example 7B under a nitrogen atmosphere followed by the addition of 817 mg of triethylsilane and the reaction mixture stirred for 1 hour at 0° C. The reaction was diluted with 125 ml of ethyl acetate and the organic phase washed with water (1×50 ml), 1M sodium hydroxide solution (1×50 ml), water (1×50 ml) and a brine solution (2×50 ml). The organic phase was dried and concentrated in vacuo to give the crude product, which was chromatographed on silica gel (ethyl acetate-hexane; 10%–90%; v:v), 1.28 g, m.p. 98°–100° C.

D. 2-(2-Phenyl-5-methyloxazol-4-ylmethyl)-5-cyanobenzofuran

A mixture of 1.28 g of the product of Example 7C and 623 mg of cuprous cyanide was treated with 10 ml of dimethylformamide and the yellow slurry heated under a nitrogen atmosphere overnight at 150° C. The mixture was cooled and poured into 15 ml of concentrated ammonium hydroxide diluted with 5 ml of water. An additional 25 ml of ammonium hydroxide was added and the mixture extracted with 200 ml of ethyl acetate. The organic phase was separated, washed with water (3×75 ml) and a brine solution (2×50 ml) and dried over sodium sulfate. The residue resulting from removal of the solvent in vacuo was chromatographed on 100 g of silica gel (ethyl acetate-hexane; 20%–80%; v:v) to give 626 mg of product, m.p. 139°–140° C.

E. 2-(2-Phenyl-5-methyloxazol-4-ylmethyl)-5-benzofurancarboxaldehyde

A mixture of 620 mg of the product of Example 7D and 620 mg of a 50% aluminum-nickel alloy in 20 ml of 70% formic acid was heated to reflux for 2 hours. The reaction was cooled and the solids filtered. The filtrate was extracted with 200 ml of ethyl acetate and the extract washed with water (2×75 ml), 1N sodium hydroxide solution, water (2×75 ml) and a brine solution (1×50 ml). The extract was dried over sodium sulfate and concentrated to give 544 mg of the desired product, m.p. 116°–118° C.

F. 5-(2-[2-Phenyl-5-methyloxazol-4-ylmethyl]benzofur-5-ylmethylidene)-2-thio-2,4-oxazolidinedione A reaction mixture comprised of 534 mg of the product of Example 7E, 296 mg of 2-thio-2,4-oxazolidinedione and 413 mg of sodium acetate in 3 ml of acetic acid was heated to reflux for 4 hours. The reaction was poured into 50 ml of water and extracted with ethyl acetate. The extract was washed with water (4×50 ml) and a brine solution (2×50 ml) and dried over sodium sulfate. Concentration of the extract gave an oil, 720 mg, which was chromatographed on 100 g of silica gel (ethyl acetate-hexane; 20%–80%; v:v followed by 50%–50%; v:v) to give the desired product containing some 2-thio-2,4-oxazolidinedione. The starting material was extracted using methanol leaving the desired product, 173 mg, m.p. 180° C. (dec.).

G. 5-(2-[2-Phenyl-5-methyloxazol-4-ylmethyl]benzofur-5-ylmethylidene)-2,4-oxazolidinedione To 170 mg of the product of Example 7F was added 3.5 ml of a solution comprised of 600 mg of potassium hydroxide, 1.5 ml of water and 9 ml of methanol and the resulting slurry cooled to 0° C. in an ice bath. To the cold slurry was added 0.35 ml of 30% hydrogen peroxide and the mixture allowed to stir at room temperature for 1.5 hours. The reaction mixture was poured into 50 ml of 0.5N hydrochloric acid and extracted with 125 ml of ethyl acetate. The extract was washed with water (2× 50 ml) and a brine solution (2×50 ml) and dried over sodium sulfate. Removal of the solvent in vacuo gave 160 mg of product, m.p. 185°–200° C.

H. 5-(2-[2-Phenyl-5-methyloxazol-4-ylmethyl]benzofur-5-ylmethyl)-2,4-oxazolidinedione A mixture of 160 mg of the product of Example 7G and 160 mg of sulfur resistant palladium-on-charcoal in 5 ml of dry tetrahydrofuran was shaken in a hydrogen atmosphere at 40 psi for 40 hours. The spent catalyst was filtered through celite and the filtrate concentrated to give 136 mg of product which was recrystallized from methanol, m.p. 190°–191° C.

Analysis calculated for $C_{23}H_{18}O_5N_2$: C, 68.7; H, 4.5; N, 7.0%. Found: C, 67.0; H, 4.5; N, 6.8%.

EXAMPLE 8

Employing the procedure of Example 7A and starting with the appropriate reagents, the following intermediates were prepared:

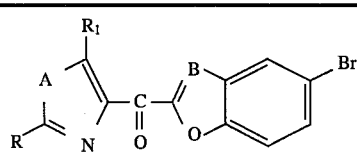

| R | $R_1$ | A | B | m.p. °C. |
|---|---|---|---|---|
| β-$C_{10}H_7$— | $CH_3$ | O | —CH= | 231–234 |
| p-$CH_3C_6H_4$— | $CH_3$ | O | —CH= | |
| m-$CH_3C_6H_4$— | $CH_3$ | O | —CH= | 173–178 |
| $C_6H_{11}$— | $CH_3$ | O | —CH= | oil |
| $C_6H_5$— | $CH_3$ | S | —CH= | |

EXAMPLE 9

Using the procedure of Example 7B and employing the appropriate reagents, the following intermediates were prepared:

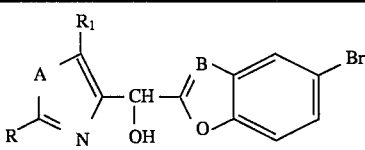

| R | $R_1$ | A | B | m.p. °C. |
|---|---|---|---|---|
| β-$C_{10}H_7$— | $CH_3$ | O | —CH= | 189–191 |
| p-$CH_3C_6H_4$— | $CH_3$ | O | —CH= | |
| m-$CH_3C_6H_4$— | $CH_3$ | O | —CH= | 133–136 |
| $C_6H_{11}$— | $CH_3$ | O | —CH= | |
| $C_6H_4$— | $CH_3$ | S | —CH= | 144–146 |

EXAMPLE 10

Starting with the requisite materials and using the procedure of Example 7C, the following intermediates were prepared:

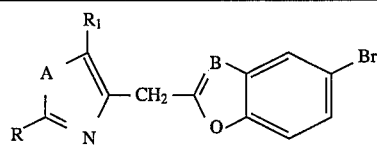

| R | $R_1$ | A | B | m.p. °C. |
|---|---|---|---|---|
| β-$C_{10}H_7$— | $CH_3$ | O | —CH= | 143–145 |
| p-$CH_3C_6H_4$— | $CH_3$ | O | —CH= | |
| m-$CH_3C_6H_4$— | $CH_3$ | O | —CH= | 88–90 |
| $C_6H_{11}$— | $CH_3$ | O | —CH= | oil |
| $C_6H_5$— | $CH_3$ | S | —CH= | 134–135 |

EXAMPLE 11

Using the procedure of Example 7D and starting with the requisite reagents, the following intermediates were prepared:

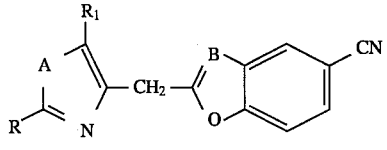

| R | $R_1$ | A | B | m.p. °C. |
|---|---|---|---|---|
| β-$C_{10}H_7$— | $CH_3$ | O | —CH= | 175–176 |
| p-$CH_3C_6H_4$— | $CH_3$ | O | —CH= | |
| m-$CH_3C_6H_4$— | $CH_3$ | O | —CH= | 125–126 |
| $C_6H_{11}$— | $CH_3$ | O | —CH= | 85–87 |
| $C_6H_5$— | $CH_3$ | S | —CH= | 134–136 |

EXAMPLE 12

Employing the procedure of Example 7E and starting with required reagents, the following intermediates were prepared:

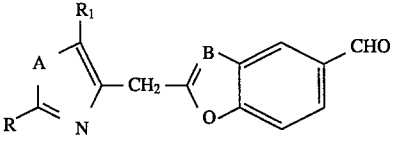

| R | $R_1$ | A | B | m.p. °C. |
|---|---|---|---|---|
| β-$C_{10}H_7$— | $CH_3$ | O | —CH= | 153–155 |
| p-$CH_3C_6H_4$— | $CH_3$ | O | —CH= | 128–129 |
| m-$CH_3C_6H_4$— | $CH_3$ | O | —CH= | |
| $C_6H_{11}$— | $CH_3$ | O | —CH= | oil |
| $C_6H_5$— | $CH_3$ | S | —CH= | 142–146 |

EXAMPLE 13

Using the procedure of Example 7F and starting with the appropriate starting reagents, the following compounds were prepared:

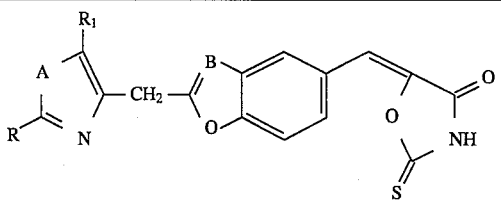

| R | R₁ | A | B | m.p. °C. |
|---|---|---|---|---|
| β-C₁₀H₇— | CH₃ | O | —CH= | 223–226 |
| p-CH₃C₆H₄— | CH₃ | O | —CH= | |
| m-CH₃C₆H₄— | CH₃ | O | —CH= | |
| C₆H₁₁— | CH₃ | O | —CH= | 208–211 |
| C₆H₅— | CH₃ | S | —CH= | |

EXAMPLE 14

Starting with the compounds of Example 13 and the other requisite starting reagents, and employing the procedure of Example 7G, the following compounds were prepared:

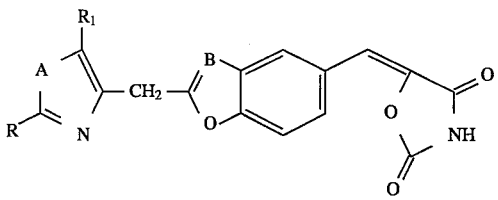

| R | R₁ | A | B | m.p. °C. |
|---|---|---|---|---|
| β-C₁₀H₇— | CH₃ | O | —CH= | |
| p-CH₃C₆H₄— | CH₃ | O | —CH= | |
| m-CH₃C₆H₄— | CH₃ | O | —CH= | |
| C₆H₁₁— | CH₃ | O | —CH= | |
| C₆H₅— | CH₃ | S | —CH= | |

EXAMPLE 15

Employing the procedure of Example 7H and starting with the products of Example 14 and necessary reagents, the following final products were prepared:

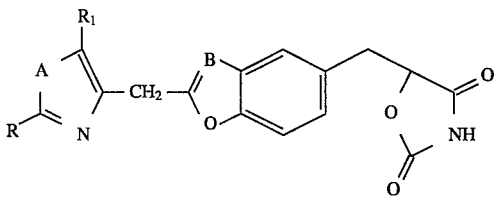

| R | R₁ | A | B | m.p. °C. |
|---|---|---|---|---|
| β-C₁₀H₇— | CH₃ | O | —CH= | 178–210 |
| p-CH₃C₆H₄— | CH₃ | O | —CH= | 184–185 |
| m-CH₃C₆H₄— | CH₃ | O | —CH= | >240 (Na salt) |
| C₆H₁₁— | CH₃ | O | —CH= | 98 |
| C₆H₄— | CH₃ | S | —CH= | 148–151 |

EXAMPLE 16

5-(2-[2-Phenyl-5-methyloxazol-4-ylmethyl]benzoxazol-5-ylmethyl)-2,4-oxazolidinedione (II: R=C₆H₅; R₁=CH₃; A=O; and B=N)

A. 5-p-Hydroxyphenyl-2,4-oxazolidinedione

To 10 ml of trifluoroacetic acid was added 500 mg of 3-triphenylmethyl-5-p-hydroxyphenyl-2,4-oxazolidinedione and the reaction mixture stirred at room temperature for 10 minutes. The reaction was poured into 50 ml of water and extracted with ethyl acetate. The organic layer was separated, washed with water (2× 40 ml) and dried over sodium sulfate. Removal of the solvent in vacuo gave a yellow solid which was recrystallized from ethyl acetate-cyclohexane, 226 mg.

B. 5-(3-Nitro-4-hydroxyphenyl)-2,4-oxazolidinedione

To 12 ml of ice cold concentrated nitric acid was added the product of Example 16A. After 5 minutes the reaction mixture was poured over 80 g of ice to give a yellow solid. The solid was extracted into ethyl acetate and the organic phase washed with water (2× 80 ml), a brine solution (1×80 ml) and dried over sodium sulfate. Removal of the solvent gave 1.55 g of the desired product.

C. 5-(3-Amino-4-hydroxyphenyl)-2,4-oxazolidinedione

A mixture of 1.98 g of the product of Example 16B and 150 mg of 10% palladium-on-charcoal in 6 ml of tetrahydrofuran was shaken in a hydrogen atmosphere for 4 hours. The spent catalyst was filtered and the filtrate concentrated to a foam.

D. 2-Phenyl-5-methyloxazol-4-ylacetic acid

To a solution of 1.0 g of 2-phenyl-4-hydroxyethyl5-methyloxazole in 20 ml of acetone was added a solution consisting of 1 g of chromium trioxide, 0.9 ml of concentrated sulfuric acid and 4 ml of water and the reaction stirred at room temperature for 40 minutes. The reaction mixture was poured into water (60 ml) and the product extracted with 150 ml of ethyl acetate. The organic layer was washed with water (2×50 ml) and dried over sodium sulfate. Removal of the solvent gave the crude product as an oil. The residue was dissolved in 80 ml of ethyl acetate and the product extracted with 100 ml of 0.25N aqueous sodium hydroxide. The aqueous layer was separated, acidified with 1N hydrochloric acid and the product extracted with 150 ml of ethyl acetate. The organic phase was separated, dried over sodium sulfate and concentrated to give a yellow solid, 500 mg.

E. 5-(2-[2-Phenyl-5-methyloxazol-4-ylmethyl]benzoxazol-5-ylmethyl)-.2,4-oxazolidinedione A mixture of 650 mg of phosphorus pentoxide, 1.64 ml of bis(trimethylsilyl)ether and 6 ml of o-dichlorobenzene was heated to 100° C. for 10 minutes followed by the addition of 255 mg of the product of Example 16C and 250 mg of the product of Example 16D. The resulting reaction mixture was heated to 150° C. for 2 hours and was then cooled and poured into water. The product was extracted with ethyl acetate, which was dried over sodium sulfate and concentrated to an oil. The residue was flash chromatographed and then recrystallized from ethyl acetate-cyclohexane, 40 mg, m.p. 196°–198° C. The NMR (300 MHz, DMSO-d₆) delta, showed absorption at 8.0–7.92 (m, 2H), 7.68 (d, 1H), 7.60 (s, 1H), 7.58–7.52 (m, 3H), 7.27 (d, 1H), 5.34 (t, 1H), 4.36 (s, 2H), 3.60–3.22 (m, 2H) and 2.52 (s, 3H).

We claim:

1. Compounds of the formulae

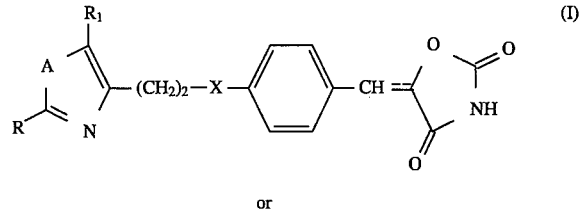

or

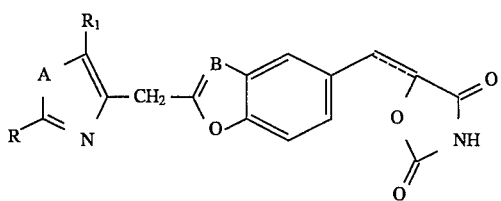

or a pharmaceutically acceptable salt thereof wherein the dotted line represents a bond or no bond, R is cycloalkyl having three to seven carbon atoms, naphthyl, thienyl, furyl, phenyl or substituted phenyl wherein said substituent is alkyl having one to three carbon atoms, alkoxy having one to three carbon atoms, trifluoromethyl, chloro, fluoro or bis(trifluoromethyl); $R_1$ is alkyl having one to three carbon atoms; X is O or C=O; A is O or S; and B is N or CH.

2. A compound of claim 1, formula I, wherein the dotted line represents no bond.

3. A compound of claim 2, wherein $R_1$ is methyl, X is O and A is O.

4. The compound of claim 3, wherein R is phenyl.

5. The compound of claim 3, wherein R is 2-naphthyl.

6. The compound of claim 3, wherein R is 3,5-bis(trifluoromethyl)phenyl.

7. A compound of claim 1, formula II, wherein the dotted line represents no bond.

8. A compound of claim 7, wherein $R_1$ is methyl and A is O.

9. The compound of claim 8, wherein R is phenyl and B is CH.

10. The compound of claim 8, wherein R is p-tolyl and B is CH.

11. The compound of claim 8, wherein R is cyclohexyl and B is CH.

12. The compound of claim 8, wherein R is m-tolyl and B is CH.

13. The compound of claim 8, wherein R is phenyl and B is N.

14. The compound of claim 8, wherein R is β-naphthyl and B is CH.

15. A pharmaceutical composition for use in a hyperglycemic mammal which comprises a blood glucose lowering amount of a compound of claim 1 and a pharmaceutically acceptable carrier.

16. A method of lowering the blood glucose in a hyperglycemic mammal which comprises administering to said mammal a blood glucose lowering effective amount of a compound of claim 1.

17. A pharmaceutical composition for use in a hypercholesterolemic mammal which comprises a blood cholesterol lowering amount of a compound of claim 1 and a pharmaceutically acceptable carrier.

18. A method of lowering the blood cholesterol in a hypercholesterolemic mammal which comprises administering to said mammal a blood cholesterol lowering effective amount of a compound of claim 1.

* * * * *